United States Patent
Vacanti et al.

(10) Patent No.: US 7,914,579 B2
(45) Date of Patent: *Mar. 29, 2011

(54) TISSUE ENGINEERED TENDONS AND LIGAMENTS

(75) Inventors: Charles A. Vacanti, Lexington, MA (US); Yi Lin Cao, Shrewsbury, MA (US); Robert S. Langer, Newton, MA (US); Joseph P. Vacanti, Winchester, MA (US); Keith Paige, Brookline, MA (US); Joseph Upton, Brookline, MA (US)

(73) Assignees: Children's Medical Center Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/351,127

(22) Filed: Feb. 9, 2006

(65) Prior Publication Data
US 2007/0005139 A1 Jan. 4, 2007

Related U.S. Application Data

(60) Division of application No. 10/913,769, filed on Aug. 6, 2004, now abandoned, which is a continuation of application No. 09/670,051, filed on Sep. 25, 2000, now Pat. No. 6,840,962, which is a division of application No. 08/905,491, filed on Aug. 4, 1997, now Pat. No. 6,123,727, which is a continuation of application No. 08/431,780, filed on May 1, 1995, now abandoned.

(51) Int. Cl.
*A61F 2/08* (2006.01)
*A61F 2/42* (2006.01)

(52) U.S. Cl. ........................................ 623/13.2

(58) Field of Classification Search .................. 623/13.2, 623/23.11, 23.12, 23.13, 23.14, 23.15, 23.16, 623/23.17, 23.18, 23.19, 23.2, 23.21, 23.22, 623/23.23, 23.24, 23.25, 23.26, 23, 27, 23.28, 623/23.29, 23.3, 23.31, 23.32, 23.33, 23.34, 623/35, 23.36, 23.37, 23.38
See application file for complete search history.

(56) References Cited

U.S. PATENT DOCUMENTS

| 1,995,970 A | 3/1935 | Dorough |
| 2,609,347 A | 9/1952 | Wilson |
| 2,653,917 A | 9/1953 | Hammon |

(Continued)

FOREIGN PATENT DOCUMENTS

AU B-24245/88 2/1989

(Continued)

OTHER PUBLICATIONS

Allcock et al., "Synthesis of Poly[(Amino Acid Alkyl Ester)Phosphazenes]" *Macromolecules* 10(4):824-830 (1977).

(Continued)

*Primary Examiner* — Thomas J Sweet
(74) *Attorney, Agent, or Firm* — Clark & Elbing LLP; Kristina Bieker-Brady

(57) ABSTRACT

Connective tissue, including neo-tendons and ligaments, has been constructed using biodegradable synthetic scaffolds seeded with tenocytes. The scaffolds are preferably formed from biodegradable fibers formed of a polymer such as polyglycolic acid-polylactic acid copolymers, and seeded with cells isolated from autologous tendon or ligament by means of enzymatic digestion or direct seeding into tissue culture dishes from explants. The cell polymer constructs are then surgically transplanted to replace missing segments of functioning tendon or ligament.

26 Claims, 1 Drawing Sheet

U.S. PATENT DOCUMENTS

| | | |
|---|---|---|
| 2,659,935 A | 11/1953 | Hammon |
| 2,664,366 A | 12/1953 | Wilson |
| 2,676,945 A | 4/1954 | Higgins |
| 2,683,136 A | 7/1954 | Higgins |
| 2,703,316 A | 3/1955 | Schneider |
| 2,758,987 A | 8/1956 | Salzberg |
| 2,846,407 A | 8/1958 | Wilson |
| 2,951,828 A | 6/1960 | Zeile et al. |
| 3,531,561 A | 9/1970 | Trehu |
| 3,826,241 A | 7/1974 | Bucalo |
| 3,880,991 A | 4/1975 | Yolles |
| 3,883,393 A | 5/1975 | Knazek et al. |
| 3,902,497 A | 9/1975 | Casey |
| 3,935,065 A | 1/1976 | Doerig |
| 3,949,073 A | 4/1976 | Daniels et al. |
| 3,960,150 A | 6/1976 | Hussain et al. |
| 3,974,526 A | 8/1976 | Dardik et al. |
| 3,992,725 A | 11/1976 | Homsy |
| 3,995,444 A | 12/1976 | Clark et al. |
| 4,026,304 A | 5/1977 | Levy |
| 4,060,081 A | 11/1977 | Yannas et al. |
| 4,069,307 A | 1/1978 | Higuchi et al. |
| 4,137,921 A | 2/1979 | Okuzumi |
| 4,141,087 A | 2/1979 | Shalaby et al. |
| 4,144,126 A | 3/1979 | Burbidge |
| 4,186,448 A | 2/1980 | Brekke |
| 4,192,827 A | 3/1980 | Mueller et al. |
| 4,205,399 A | 6/1980 | Shalaby et al. |
| 4,228,243 A | 10/1980 | Iizuka |
| 4,239,664 A | 12/1980 | Teng et al. |
| 4,243,775 A | 1/1981 | Rosensaft et al. |
| 4,277,582 A | 7/1981 | Mueller et al. |
| 4,280,954 A | 7/1981 | Yannas et al. |
| 4,304,591 A | 12/1981 | Mueller et al. |
| 4,304,866 A | 12/1981 | Green et al. |
| 4,328,204 A | 5/1982 | Wasserman et al. |
| 4,347,847 A | 9/1982 | Usher |
| 4,348,329 A | 9/1982 | Chapman |
| 4,352,883 A | 10/1982 | Lim |
| 4,356,261 A | 10/1982 | Kuettner |
| 4,391,797 A | 7/1983 | Folkman et al. |
| 4,416,986 A | 11/1983 | Markus et al. |
| 4,427,808 A | 1/1984 | Stol et al. |
| 4,431,428 A | 2/1984 | Schmer |
| 4,438,198 A | 3/1984 | Schmer |
| 4,439,152 A | 3/1984 | Small |
| 4,440,921 A | 4/1984 | Allcock et al. |
| 4,444,887 A | 4/1984 | Hoffmann |
| 4,446,229 A | 5/1984 | Indech |
| 4,446,234 A | 5/1984 | Russo et al. |
| 4,450,150 A | 5/1984 | Sidman |
| 4,456,687 A | 6/1984 | Green |
| 4,458,678 A | 7/1984 | Yannas et al. |
| 4,485,096 A | 11/1984 | Bell |
| 4,485,097 A | 11/1984 | Bell |
| 4,489,056 A | 12/1984 | Himmelstein et al. |
| 4,494,385 A | 1/1985 | Kuraoka et al. |
| 4,495,174 A | 1/1985 | Allcock et al. |
| 4,505,266 A | 3/1985 | Yannas et al. |
| 4,520,821 A | 6/1985 | Schmidt et al. |
| 4,528,265 A | 7/1985 | Becker |
| 4,544,516 A | 10/1985 | Hughes et al. |
| 4,545,082 A | 10/1985 | Hood |
| 4,553,272 A | 11/1985 | Mears |
| 4,559,298 A | 12/1985 | Fahy |
| 4,559,304 A | 12/1985 | Kasai et al. |
| 4,563,350 A | 1/1986 | Nathan et al. |
| 4,563,490 A | 1/1986 | Stol et al. |
| 4,576,608 A | 3/1986 | Homsy |
| 4,595,713 A | 6/1986 | St. John |
| 4,609,551 A | 9/1986 | Caplan et al. |
| 4,627,853 A | 12/1986 | Campbell et al. |
| 4,637,931 A | 1/1987 | Schmitz |
| 4,642,120 A | 2/1987 | Nevo et al. |
| 4,645,669 A | 2/1987 | Reid |
| 4,675,189 A | 6/1987 | Kent et al. |
| 4,675,284 A | 6/1987 | Leevy et al. |
| 4,713,070 A | 12/1987 | Mano |
| 4,721,096 A | 1/1988 | Naughton et al. |
| 4,734,373 A | 3/1988 | Bartal |
| 4,757,017 A | 7/1988 | Cheung |
| 4,757,128 A | 7/1988 | Domb et al. |
| 4,778,749 A | 10/1988 | Vasington et al. |
| 4,846,835 A | 7/1989 | Grande |
| 4,853,324 A | 8/1989 | Viles et al. |
| 4,868,121 A | 9/1989 | Scharp et al. |
| 4,880,622 A | 11/1989 | Allcock et al. |
| 4,891,225 A | 1/1990 | Langer et al. |
| 4,946,938 A | 8/1990 | Magill et al. |
| 4,963,489 A | 10/1990 | Naughton et al. |
| 4,988,761 A | 1/1991 | Ikada et al. |
| 5,019,087 A | 5/1991 | Nichols |
| 5,032,508 A | 7/1991 | Naughton et al. |
| 5,041,138 A | 8/1991 | Vacanti et al. |
| 5,078,744 A * | 1/1992 | Chvapil ..................... 606/86 |
| 5,092,887 A | 3/1992 | Gendler |
| 5,171,273 A | 12/1992 | Silver et al. |
| 5,263,984 A | 11/1993 | Li et al. |
| 5,306,311 A | 4/1994 | Stone et al. |
| 5,376,118 A | 12/1994 | Kaplan et al. |
| 5,595,621 A | 1/1997 | Light et al. |
| 5,681,353 A * | 10/1997 | Li et al. ................. 623/14.12 |
| 5,696,175 A * | 12/1997 | Mikos et al. ................... 521/61 |
| 5,716,404 A | 2/1998 | Vacanti et al. |
| 6,027,743 A | 2/2000 | Khouri et al. |

FOREIGN PATENT DOCUMENTS

| | | |
|---|---|---|
| DE | 2853614 | 7/1979 |
| DE | 3518150 | 10/1986 |
| EP | 0153896 | 9/1985 |
| EP | 0 226 061 | 6/1987 |
| EP | 0248246 | 12/1987 |
| EP | 0248247 | 12/1987 |
| EP | 0 282 746 | 9/1988 |
| EP | 0 339 607 | 11/1989 |
| JP | 62-11459 | 1/1987 |
| JP | 63074498 | 4/1988 |
| JP | 63196273 | 8/1988 |
| JP | 63196595 | 8/1988 |
| WO | WO 87/06120 | 10/1987 |
| WO | WO 88/03785 | 6/1988 |
| WO | WO 89/00413 | 1/1989 |
| WO | WO 89/07944 | 8/1989 |
| WO | WO 90/12603 | 11/1990 |
| WO | WO 90/12604 | 11/1990 |
| WO | WO 92/07525 | 5/1992 |
| WO | WO 93/08850 | 5/1993 |
| WO | WO 93/17913 | 9/1993 |
| WO | WO 94/21299 | 9/1994 |
| WO | WO 94/25079 | 11/1994 |

OTHER PUBLICATIONS

Allcock et al., "Hydrolysis Pathways for Aminophosphazenes" *Inorg. Chem.* 21(1):515-521 (1982).

Allcock et al., "Amphilphilic Polyphosphazenes as Membrane Materials: Influence of Side Group on Radiation Cross Linking," *Biomaterials* 9(6):500-508 (1988).

Allcock et al., "Phosphonitrilic Compounds. IV. High Molecular Weight Poly[bis(amino)phosphazenes] and Mixed-Substituent Poly(aminophosphazenes)," *Inorg. Chem.* 11(11):2584-2590 (1972).

Allcock et al., "Polyphosphazenes with Etheric Side Groups; Prospective Biomedical and Solid Electrolyte Polymers" *Macromolecules* 19:1508-1512 (1986).

Allcock and Kwon, "An Ionically Cross-Linkable Polyphosphazene: Poly[bis(carboxylatophenoxy)phosphazene] and Its Hydrogels and Membranes" *Macromolecules* 22:75-79 (1989).

Allcock and Kwon, "Glyceryl Phosphazenes: Synthesis, Properties, and Hydrolysis" *Macromolecules* 21(7):1980-1985 (1988).

Allcock and Scopelianos, "Synthesis of Sugar Substituted Cyclic and Polymeric Phosphazenes and Their Oxidation, Reduction, and Acetylation Reactions" *Macromolecules* 16(5):715-719 (1983).

Anderson et al., "Gene Expression in Implanted Rat Hepatocytes Following Retroviral-Mediated Gene Transfer" *Somatic Cell and Mol. Gen.* 15(3):215-227 (1989).

Anderson, Caltech Biology (1987).
Alberts et al., Molecular Biology of the Cell, Garland Publishing, Inc., pp. 893-894.
Atala et al., "Endoscopic Treatment of Vesicoureteral Reflux with a Chondrocyte-Alginate Suspension" *J. Urology* 152:641-643 (1994).
Atala et al., "Endoscopic Treatment of Vesicoureteral Reflux with a Self-detachable Balloon System" *J. Urology* 148:724-728 (1992).
Atala et al., "Injectable Alginate Seeded with Chondrocytes as a Potential Treatment for Vesicoureteral Reflux" *J. Urology* 150:745-747 (1993).
Atala et al., "Laparoscopic Correction of Vesicoureteral Reflux" *J. Urology* 150:748-751 (1993).
Atala et al., "Sonography with Sonicated Albumin in the Detection of Vesidoureteral Reflux" *J. Urology* 150:756-758 (1993).
Baklund et al., "Toward a Transplantation Therapy in Parkinson's Disease" *Ann.N.Y. Acad. Sci*. 495: 658-673 (1987).
Bazeed et al., New Surgical Procedure for Management of Peyronie Disease *Urology* 21(5):501-504 (1983).
Ben-Ze'ev et al., "Cell-Cell and Cell-Matrix Interactions Differentially Regulate the Expression of Hepatic and Cytoskeletal Genes in Primary Cultures of Rat Hepatocytes" *Proc. Natl. Acad. Sci. USA* 85:2161-2165 (1988).
Bennett and Hirt, "A History of Tissue Expansion" *Dermatol. Surg. Oncol.* 19:1066-1073 (1993).
Berrino et al., "Surgical Correction of Breast Deformities Following Long-Lasting Complications of Polyurethane-Covered Implants" *Ann. Plast. Surg.* 24:481 (1990).
Biers, "Organogenesis' Human Artery Equivalent May Revolutionize Vascular Grafts" *Gen. Engineering News* (1987).
Bissell et al., "Interactions of Rat Hepatocytes with Type IV Collagen, Fibronectin and Laminin Matrices, Distinct Matrix-Controlled Modes of Attachment and Spreading" *Eur. J. Cell Biol.* 40:72-78 (1986).
Bissell et al., "The Role of Extracellular Matrix in Normal Liver" *Scand. J. Gastroenterol.* 23:1-7(1988).
Bissell, "Support of Cultured Hepatocytes by a Laminin-Rich Gel," *J. Clin. Invest.* 79:801-812 (1987).
Bjorklund, *Ann. N.Y. Acad. Sci.* 495:676-686 (1987).
Blaivas et al., "When Sphincter Failure is the Cause of Female Stress Incontinence," *Contemporary Urology* 5(3): 33-54 (1993).
Bohn et al., "Adrenal Medulla Grafts Enhance Recovery of Striatal Dopaminergic Fibers," *Science* 238(4817): 913-916 (1987).
"Brain Graft Seeks to Relieve Huntington Disease Patient" *New York Times* (1988).
Brown, "Fibrin-Collagen Nerve Repair Device," Inventors: Russ Griffiths, Larry Stensaas and Ken Horch, Letter dated (1988).
Burke, "The Effects of the Configuration of an Artificial Extracellular Matrix on the Development of a Functional Dermis" *The Role of Extracellular Matrix in Development* 351-355 (1984).
Cao et al., "Generation of Neo-Tendon Using Synthetic Polymers Seeded with Tenocytes" *Trans. Proc.* 6:3390-3392 (1994).
Chaikin, "Tissue Engineering: Science Non-Fiction" *Medical Industry Executive* pp. 6-7 (1993).
Chuang et al.. "Sheath Needle for Liver Biopsy in High-Risk Patients" *RSNA* 261-262 (1988).
Cilento et al., "Phenotypic and Cytogenetic Characterization of Human Bladder Urothelia Expanded in Vitro" *Micro. Immunol.* 152: 665-670 (1994).
Claes et al., "Pulmonary Migration Following Periurethral Polytetrafluorethylene Injection of Urinary Incontinence" *J. Urology* 142:821-822 (1989).
Cohen, "Navigating Through Tissue Expansion Terminology" *J. Dermatol. Surg. Oncol.* 19:614-615 (1993).
Cosimi et al., "Transplantation of Skin" *Surgical Clinics of N.A.* 58(2):435-451 (1978).
Collier et al., "Norepinephrine Deficiency and Behavioral Senescence in Aged Rats: Transplanted Locus Ceruleus Neurons as an Experimental Replacement Therapy" *Ann. N.Y. Acad. of Sci.* 495:396-403 (1987).
Culliton, "Gore Tex Organoids and Genetic Drugs" *Science* 246:747-749 (1989).

da Silva, "An in Vivo Model to Quantify Motor and Sensory Peripheral Nerve Regeneration Using Bioresorbable Nerve Guide Tubes" *Brain Res.* 342:307-315 (1985).
Davis et al., "Human Amnion Membrane Serves as a Substratum for Growing Axons In Vitro and In Vivo" *Science* 236:1106-1109(1987).
del Cerro et al., "Retinal Transplants into One Anterior Chamber of the Rat Eye" *Neuroscience* 21(3):707-723 (1987).
Doillon et al., "Collagen-Based Wound Dressings: Control of the Pore Structure and Morphology" *J. Bio. Mat. Res.* 20:1219-1228 (1986).
Doillon et al. "Epidermal Cells Cultured on a Collagen-Based Material" *G.W. Bailey, Editor, Proceedings of the 44th Annual Meeting of the Electron Microscopy Society of America* 212-213 (1986).
Ebata et al., "Liver Regeneration Utilizing Isolated Hepatocytes Transplanted into the Rat Spleen" *Surg. Forum* 29:338-340 (1978).
Elkowitz et al., "Various Methods of Breast Reconstruction After Mastectomy: An Economic Comparison" *Plastic Recon. Surg.* 92(1):77-83 (1993).
Erickson, "Material Help" *Scientific American* pp. 114-116 (1992).
Ferro et al., "Periurethral Granuloma Unusual Complication of Teflon Periurethral Injection" *Urology* 31(5):422-423 (1988).
Folkman et al., "Angiogenic Factors" *Science* 235:442-447 (1987).
Fontaine et al., "Optimization Studies on Retroviral Mediated Gene Transfer into Rat Hepatocytes: Implications for Gene Therapy" The Society of University Surgeons, Resident's Program, Cincinnati, OH (1992).
Freed et al., "Neoccartilage Formation In Vitro and In Vivo Using Cells Cultured on Synthetic Biodegradable Polymers" *J. Bio. Mat. Res.* 27:11-23 (1993).
Freshney, "The Culture Environment: I. Substrate, Gas Phase, and Temperature" *Culture of Animal Cells* pp. 55-66 Alan R. Liss, NY (1983).
Gash et al., "Amitotic Neuroblastoma Cells Used for Neural Implants in Monkeys" *Science* 233(4771):1420-1422 (1986).
Gash, "Neural Transplantation: Potential Therapy for Alzheimer's Disease" *J. Neural Trans.* [ *Suppl*] 24:301-308 (1987).
Geiss et al., "Multicenter Survey of Endoscopic Treatment of Vesidoureteral Reflux in Children" *Eur. Urol.* 17:383-329 (1990).
Gilbert et al., "Cell Transplantation of Genetically Altered Cells on Biodegradable Polymer Scaffolds in Syngeneic Rats" Department of Surgery. The Children's Hospital and Harvard Medical School, Boston, MA.
Grande et al., "Healing of Experimentally Produced Lesions in Rabbit Articular Cartilage by Autologous Chondrocyte Transplantation" *The Anatomical Record* 218:142-148 (1987).
Grande et al., "The Repair of Experimentally Produced Defects in Rabbit Articular Cartilage by Autologous Chondrocyte Transplantation" *J Orthop Res.* 7(2):208-218 (1989).
Green, "Growth of Cultured Human Epidermal Cells into Multiple Epithelia Suitable for Grafting" *Proc. Natl. Acad. Sci. USA* 76(11):5665-5668 (1979).
Grolleman et al., "Studies on Bioerodible Drug Carrier System Based on Polyphosphazene" *J. Controlled Release* 3:143-154 (1986).
Groth et al., "Correction of Hyperbilirubinemia in the Glucoronyltransferase-Deficient Rat by Intraportal Hepatocyte Transplantation" *Transplant Proc.* 9:313-316 (1977).
Hammond et al.. "Morphologic Analysis of Tissue-Expander Shape Using a Biochemical Model" *Plastic and Reconstructive Surgery* 92(2):255-259 (1993).
Harris et al., "Silicone Rubber Substrate: A New Wrinkle in the Study of Cell Locomotion" *Science* 208:177-179 (1980).
Hendren and Atala, "Use of Bowel for Vagina Reconstruction" *J. Urology* 152:752-755 (1994).
Henly et al., "Particular Silicone of Use in Periurethral Injections: A Study of Local Tissue Effects and a Search for Migration" *J. Urology* 147(4): 376A (1992).
Henry et al., "Nerve Regeneration Through Biodegradable Polyester Tubes" *Exp. Neurol.* 90(3):652-676 (1985).
Ingber et al., "Cells as Tensecrity Structures: Architectural Regulation of Histodifferentiation by Physical Forces Transduced Over Basement Membrane" Gene Expression During Normal and Malignant Differentiation, Anderson at al., editors pp. 13-32, Academic Press, Orlando, FL (1985).

Ingber et al., "Endothelial Growth Factors and Extracellular Matrix Regulate DNA Synthesis Through Modulation of Cell and Nuclear Expansion" In Vitro *Cell. Dev. Bio.* 23(5)387-394 (1987).

Ingber et al., "Control of Capillary Morphogenesis: A Molecular System of Mechanical Switches" *J. Cell Biol.* 107:797a (1988).

Ingber, "How Does Extracellular Matrix Control Capillary Morphogenesis?" *Cell* 58:803-805 (1989).

Ingber, "Growth Control Through Fibronectin-Dependent Modulation of Cell Shape" *J. Cell Biol.* 105:219a (1987).

Ingber et al., "Mechanochemical Switching Between Growth Factor-Stimulated Angiogenesis In Vitro:Role of Extacellular Matirix," *J.Cell. Biol.*, 109(1):317-330 (1989).

Jacksic et al., "The Use of 'Artificial Skin' for Burns" *Ann. Rev. Med.* 38:107-116 (1987).

Jauregui et al., "Attachment and Long Term Survival of Adult Rat Hepatocytes in Primary Monolayer Cultures: Comparison of Different Substrata and Tissue Culture Medial Formulations" *In Vitro Cell. Dev. Bio.* 22(1):13-22 (1986).

Jones, "Degradation of Artificial Tissue Substrates" *Cancer Invasion and Metastesis: Biologic and Therapeutic Aspects* 177-185, Raven Press, NY (1984).

Kenna et al., "Diffusion of Antibiotics Across Tissue Expanders: An in Vitro Study" *Ann. Plastic Surg.* 32(4):346-349 (1994).

Klagsbrun, "Large-Scale Preparation of Chondrocytes" *Methods in Enzymology* vol. LVIII, Academic Press, NY (1979).

Kleinman et al., "Use of Extracellular Matrix Components and Cell Culture" *Anal. Biochem.* 166:1-13 (1987).

Klompmaker et al., "Porous Polymer Implants for Repair of Full-Thickness Defects of Articular Cartilage: An Experimental Study in Rabbit and Dog" *Biomaterials* 13(9):625-634 (1992).

Kolata, "Parkinson Procedure: Fervor Turns to Disillusion" The New York Times (1988).

Kordower et al., "An In Vivo and In Vitro Assessment of Differentiated Neuroblastoma Cells as a Source of Donor Tissue for Transplantation" *Ann. N.Y. Acad.Sci.* 495:606-622 New York (1987).

Kordower et al., "Neuroblastoma Cells in Neural Transplants: A Neuroanatomical and Behavioral Analysis" *Brain Res.* 417:85-98 (1987).

Kretschmer at al., "Autotransplantation of Pancreatic Fragments to the Portal Vein and Spleen of Total Pancreatectomized Dogs" *Ann. Surg.* 187:79-86 (1978).

Kusano et al., "Proliferation Activities of Intrasplenic Hepatocytes and the Influence of Hepatotrophic Factors" *Acta Japoni Hepato* 63:345-351 (1989).

Langer and Moses, "Biocompatible Controlled Release Polymers for Delivery of Polypeptides and Growth Factors," *J. Cell. Biochem.* 45:340-345, 1991.

Langer and Vacanti, "Tissue Engineering," *Science* 260:920-926, 1993.

Leonard et al., "Endoscopic Injection of Glutaraldehyde Cross-Linked Bovine Dermal Collagen for Correction of Vesidoureteral Reflux," *J. Urology* 145:115-119, 1991.

Leong et al., "Bioerodible Polyanhydrides as Drug-Carrier Matrices I: Characterization, Degradation and Release Characteristics," *J. Bio. Mat. Res.* 16:941-955, 1985.

Letourneau, "Possible Roles of Cell-Sutstratus Adhesion of Neuronal Morphogenesis," *Dev. Biol.* 44:77-91, 1975.

Lewin, "Cloud Over Parkinson's Therapy," *Science News* 240:390-392, 1988.

Lewin, "Disappointing Brain Graft Results," *Science* 240(4858):1407, 1988.

Li, et al., "Influence of a Reconstituted Basement Membrane and its Components of Casein Gene Expression and Secretion in Mouse Mammary Epithelial Cells," *Proc. Natl. Acad. Sci. U.S.A.*, 84:136-140, 1987.

Lucas, et al., "Ectopic Induction of Cartilage and Bone by Water-Soluble Proteins from Bovine Bone Using a Polyanhydride Delivery Vehicle." *J. Bio. Mat. Res.* 24(7): 901-911, 1990.

Macklis, et al., "Cross-Linked Collagen Surface for Cell Culture that is Stable, Uniform, and Optically Superior to Conventional Surfaces," In Vitro *Cel.Develop. Biol.* 21(3):189-194,1985.

Madison et al., "Increased Rate of Peripheral Nerve Regeneration Using Bioresorbable Nerve Guides and Lamin-Containing Gel," *Exp. Neruol.* 88(3) 767-772, 1985.

Madison et al., "Nontoxic Nerve Guide Tubes Support Neovascular Growth in Transected Rat Optic Nerve," *Exp. Neurol.* 86:448-461, 1984.

Madison et al., "Peripheral Nerve Regeneration with Entubulation Repair: Comparison of Biodegradable Nerve Guides Versus Polyethylene Tubes and the Effects of a Laminin-Containing Gel," *Exp. Neurol.* 95(2):378-390, 1987.

Malizia et al., "Migration and Granulomatous Reaction After Periurethral Injection of Polytef (Teflon)," *JAMA* 251(24):3277-3281, 1984.

Marciano and Gash, "Structural and Functional Relationships of Grafted Vasopressin Neurons," *Brain Res.* 370(2): 338-342, 1986.

Matas et al., "Hepatocellular Transplantation of Metabolic Deficiencies: Decrease of Plasma Bilirubin in Gunn Rates," *Science* 192:892-894, 1976.

Matouschek, "Die Behandlung des vesikorenalen Refluxes durth Transurethrale Einspritzung von Teflonpaste," *Urologe A.* 20:263-264, 1981.

Mesnil et al., "Cell Contact but Not Junctional Communication (Dye Coupling) with Biliary Epithelial Cells is Required for Hepatocytes to Maintain Differentiated Functions," *Exper. Cell Res.* 173:524-533, 1987.

Michalopoulos and Pitot, "Primary Culture of Parenchymal Liver Cells on Collagen Membranes," *Exp. Cell Res.* 94:70-78, 1975.

Millaruelo, "Role of Plasminogen Activator and its Inhibitors on Axonal Outgrowth and Regeneration In Vivo," *Caltech Biology*, 1987.

Minato et al., "Transplantation of Hepatocytes for Treatment of Surgically Induced Acute Hepatic Failure in the Rat," *Eur. Surg. Res.* 16:162-169, 1984.

Mittleman and Marraccini, "Pulmonary Teflon Granulomas Following Periurethral Teflon Injection for Urinary Incontinence" *Arch. Pathol. Lab. Med.* 107:611-612, 1983.

Mito et al., "Hepatocellular Transplantation," Department of Surgery, Asahikawa Medical College 078 4-5 Nishi-Kagura, Asahikawa, Japan.

Mooney, "Control of Hepatocyte Function Through Polymer-Substrate Modulation," Thesis Proposal—Department of Chemical Engineering, Massachusetts Institute of Technology, 1989.

Mooney, "Switching from Differentiation to Growth in Hepatocytes: Control by Extracellular Matrix," *J. Cell. Phys.* Revised MS #7789151(3) 497-505, 1992.

Mooney, "Integrating Cell Transplantation and Controlled Drug Delivery Technologies to Engineer Liver Tissue," (abstract) *Materials Research Society*, 1995.

Mounzer et al., "Polyglycolic Acid Mesh in Repair of Renal Injury," *Urology* 28(2):172-180, 1986.

Movitz, "Accessory Spleens and Experimental Splenosis Principles of Growth," *The Chicago Medical School Quarterly* 26(4):183-187, 1967.

Naji et al., "Successful Islet Transplantation in Spontaneous Diabetes," *Surgery* 86:218-226, 1979.

Nastelin, "Pancreatic Islet Cell Transplantation: Optimization of Islet Cell Adhesion by Altering Polymer Surface Characteristics," Harvard-MIT Divisional of Health Sciences and Technology, 1990.

Naughton et al., "Granulopoiesis and Colony Stimulating Factor Production in Regenerating Liver," *Exp. Hematol.* 10(5):451-458, 1982.

Naughton et al., "Long-Term Growth of Rat Bone Marrow Cells in a Three-Dimensional Matrix," Medical Laboratory Sciences Department, Hunter College School of Health Sciences, New York, *The Anatomical Record* 218(1):97a, 1987.

Naughton et al., "Erythropoietin Production by Macrophages in the Regenerating Liver," *J. Sur. Onc.* 30:184-197, 1985.

Notter et al., "Neuronal Properties of Monkey Adrenal Medulla In Vitro," *Cell Tissue Res.* 244(1):69-76, 1986.

Nyilas et al., "Peripheral Nerve Repair with Bioresorbable Prosthese," *Trans. Am. Soc. Artif. Intern. Organs* 29:307-313, 1983.

O'C Hamilton, "Miracle Cures May Be in Your Cells," *Business Week*, 1993.

O'Connor et al., "Grafting of Burns with Cultured Epithelium Prepared from Autologous Epidermal Cells," *The Lancet* I(8210):75-78, 1981.
O'Donnell and Puri, "Treatment of Vesicoureteric Reflux by Endoscopic Injection of Teflon," *British Med. J.* 289:7-9, 1984.
Oellrich et al., "Biliary Atresia," *Neonatal Network* pp. 25-30, 1987.
Oliwenstein, "The Power of Plastics," *Discover* p. 18, 1989.
Omery, "A Nursing Perspective of the Ethical Issues Surrounding Liver Transplantation," *Heart Lung* 17(6):626-630, 1988.
Pasik, *Ann. N.Y. Acad. Sci.* 495:674-675, 1987.
Patterson and Gage, "Adrenal Chromaffin Cell-Derived Cholinergic Neurons for Brain Transplants," *Caltech Biology* pp. 201-202, 1987.
Perlow, "Brain Grafting as a Treatment for Parkinson's Disease," *Neurosurgery* 20(2):335-342, 1987.
Pimpl et al., "Experimentelle Studie zur Frage der Transplantatkonditionierung and Transplantatgrofe bei heterotoper autologen Milztransplantation," *Lagenbecks Arch.* pp. 37215-37218, 1984.
Pimpl et al., "Perfusion of Autologous Splenic Grafts in Correlation with Specific Immunological Functions an Experimental Study in Pigs," *Eur. Surg. Res.* 19:53-61, 1987.
Pitman et al., "The Use of Adhesives in Chondrocyte Transplantation Surgery: In-Vivo Studies." *Bulletin of the Hospital for Joint Diseases Orthopaedic Institute* 49(2):213-22D, 1989.
Ptasinska-Urbanska et al., "Intrascleral Introduction of Isolated Allogeneic Chondrocytes Capable of Cartilage Reformation in Rabbits: Possible Procedure in Treatment of Detachment of the Retina," *Exp. Eve. Res.* 34(3)241-247, 1977.
Puelacher et al., "Tissue-Engineered Growth of Cartilage: The Effect of Varying the Concentration of Chondrocytes Seeded onto Synthetic Polymer Matrices," *Int. J. Oral Maxillofac. Surg.* 23:49-53, 1994.
Rames and Aaronson, "Migration of Polytef Paste to the Lung and Brain Following Intravesical Injection for the Correction of Reflux," *Pediatric Surgery* 6(1):239-240, 1991.
Redmond Jr. et al., "Fetal Neuronal Grafts in Monkeys Given Methyphenyltetrahydropyridine," *The Lancet* pp. 1125-1127, 1986.
Redmond Jr. et al., "Transplants of Primate Neurons," *The Lancet* 2(8510):1046, 1986.
Reid et al., "Long-Term Cultures of Normal Rat Hepatocytes on Liver Biomatrix," *Ann. NY Acad. Sci.* 349:70-76, 1980.
Retik et al., "Management of Severe Hypospadias with 2-Stage Repair," *J. Urology* 152:74951, 1994.
Rhine et al., "Polymers for Sustained Macromolecule Release: Procedures to Fabricate Reproducible Delivery Systems and Control Release Kinetics," *J. Pharm. Sciences* 69(3):265-269, 1980.
Rosen, "Bioerodible Polymers for Controlled Release Systems," *Controlled Biomaterials Release Systems: Fabrication Technology* II: 83-110.
Rosen, "Biorodible Plyanhydrides for Controlled Drug Delivery," *Biomaterials* 2:131-133, 1883.
Sapozhnikova et al., "Morphological Changes in Splenic Autografts Following Splenectomy: Experimental and Clinical Findings," *Biological Abstracts* 86(76896), 1987.
Sasaki, "Neovascularization in the Splenic Autograft Transplanted into Rat Omentum as Studied by Scanning Electron Microscopy of Vascular Cases," *Virchows Arch.* 409:325-334, 1986.
Sawada et al., "Effects of Extracellular Matrix Components on the Growth and Differentiation of Cultured Rat Hepatocytes," *In Vitro Cell.Dev. Biol.* 23(4):267-273, 1987.
Schmeck Jr., "Doctors Try to Capitalize on the Liver's Ability to Regenerate Itself," *The New York Times Medical Science*, 1989.
Schubert et al., "Multiple Influences of a Heparin-Binding Growth Factor for Neuronal Development," *J. Cell Biology* 104:635-643,1987.
Seckel, "Nerve Regeneration Through Synthetic Biodegradable Nerve Guides: Regulation by the Target Organ," *Plast. Reconstr. Surg.* 74(2):173-181, 1974.
Selden et al., "The Pulmonary Vascular Bed as a Site for Implantation of Isolated Liver Cells in Inbred Rats," *Transplantation* 38(1):81-83, 1984.
Shine et al., "Cultured Peripheral Nervous System Cells Support Peripheral Nerve Regeneration Through Tubes in the Absence of Distal Nerve Stump," *J. Neuro. Res.* 14:393-401, 1985.
Shinoka et al., "Tissue Engineering Heart Valves: Valve Leaflet Replacement Study in a Lamb Model," *Ann. Thorac. Surg.* 60:S513-516, 1995.
Siegel and Langer, "Controlled Release of Polypeptides and Other Macromolecules," *Pharm. Res.* pp. 2-10, 1984.
Sirica et al., "Fetal Phenotypic Expression by Adult Rat Hepatocytes on Collagen Gel/Nylon Meshes," *Proc. Natl. Acad. Sci. U.S.A.* 76(11:283-287, 1979.
Sirica et al., "Use of Primary Cultures of Adult Rat Hepatocytes on Collagen Gel-Nylon Mesh to Evaluate Carcinogen-Induced Unscheduled DNA Synthesis," *Cancer Res.* 40:3259-3267, 1980.
Sladek Jr. et al., "Reversal of Parkinsonism by Fetal Nerve Cell Transplants in Primate Brain," *Ann. N.Y. Acad. Sci.* 495:641-657, 1987.
Sladek Jr. et al., "Survival and Growth of Fetal Catecholamine Neurons Transplanted Into Primate Brain," *Brain Res. Bull.* 17:809-818, 1986.
Sladek and Shoulson, "Neural Transplantation: A Call for Patience Rather than Patents" *Science* 240:386-388, 1988.
Sladek, "Transplantation of Fetal Dopamine Neurons in Primate Brain Reverses MPTP Induced Parkinsonism," *Prog. Brain Res.* 71:309-323, 1987.
Sommer et al., "Hepatocellular Transplantation for Treatment of D-Galactosamine-Induced Acute Liver Failure in Rats," *Transplant Proc.* 11(1):578-584, 1979.
Stemple, "A Factor that Induces Adrenergic Differnization in a Non Neural Crest Cell," *Caltech Biology*, 1987.
Strom et al., "Isolation, Culture, and Transplantation of Human Hepatocytes," *JNCI* 68(5):771-778, 1982.
Sudharkaran et al., "Modulation of Protein Synthesis and Secretion by Substratum in Primary Cultures of Rat Hepatocytes," *Exp. Cell Res.* 167:505-516, 1986.
Sullivan, "Spinal Injury Research Yields a Glimmer of Hope," *The New York Times* p. C6, 1987.
Sutherland et al., "Hepatocellular Transplantation in Acute Liver Failure," *Surgery* 82(1):124-132, 1977.
Tachibana, "Ureteral Replacement Using Collagen Sponge Tube Grafts," *J. Urology* 133(4):866-869, 1985.
Tavassoli et al., "Studies on Regeneration of Heterotopic Splenic Autotransplants," *Blood* 41(5):701-709, 1973.
Thompson, "Heparin-Binding Growth Factor 1 Induces the Formation of Organoid Neovascular Structures in Vivo," *Proc. Natl. Acad. Sci. U.S.A.* 86:7928-7932, 1989.
Thompson, "Implantable Bioreactors: Modern Concepts of Gene Therapy," *Current Communications in Molecular Biology*, Daniel Marshak et al., editors, pp. 143-147, Cold Spring Harbor Laboratory, 1989.
Thuroff et al., "Cultured Rabbit Vesical Smooth Muscle Cells for Lining of Dissolvable Synthetic Prosthesis," *Urology* 21(2):155-158, 1983.
Tomomura et al., "The Control of DNA Synthesis in Primary Cultures of Hepatocytes From Adult and Young Rats: Interactions of Extracellular Matrix Components, Epidermal Growth Factors, and the Cell Cycle," *J. Cell. Physiol.* 130:221-227, 1987.
Unipoint Industries, Inc., "Polyvinyl Alcohol Foam for Surgical and Industrial Use," Product Review.
UNOS Update, "National Cooperative Transplantation Study Completed," 7(10), 1991.
Upton et al., "Neocartilage Derived from Transplanted Perichondrium: What is it?" *Plast. Recon. Surgery* 68(2):166-174, 1981.
Vacanti, "Beyond Transplantation," *Arch. Surgery* 123:545-549, 1988.
Vacanti et al., "Engineered Bone from Polyglycolic Acid Polymer Scaffold and Periosteum," (abstract) *Materials Science Research Society*, 1985.
Vacanti et al., "Selective Cell Transplantation Using Bioabsorbable Artificial Polymers as Matrices," J. Ped. Surg. 23:3-9, 1988.
Vacanti et al., "Synthetic Polymers Seeded with Chondrocytes Provide a Template for New Cartilage Formation," *Plastic Reconstr. Surg.* 753-759, 1991.

Van der Kwast at al., "Establishment and Characterization of Long-Term Primary Mouse Urothelial Cell Cultures," *Urological Res.* 17(1):290-293, 1989.

Vargo, "Infection as a Complication of Liver Transplant," *Critical Care Nurse* 9(4):52-62, 1989.

Vijg et al., "UV-Induced DNA Excision Repair in Rat Fibroblasts During Immortalization and Terminal Differentiation in Vitro," *Exp. Cell Res.* 167:517-530, 1986.

Vorstman et al., "Polytetrafluoroethylene Injection for Urinary Incontinence in Children," *J. Urology* 133(2):248-250, 1985.

Vroeman et al., "Hepatocyte Transplantation for Enzyme Deficiency Disease in Congenic Rats," *Transplantation* 42(2):130-135, 1986.

Walker et al., "Injectable Bioglass as a Potential Substitute for Injectable Polytetrafluoroethylene," *J. Urology* 148(1):645-647.

Walton and Brown, "Tissue Engineering of Biomaterials for Composite Reconstruction: An Experimental Model," *Ann. Plastic Surg.* 30(2):104-110, 1993.

Whitaker, "Scientists Growing Tissue from 'Seed,'" *The Boston Globe*, 1993.

Wozney at al., "Novel Regulators of Bone Formation: Molecular Clones and Activities," *Science* 242:1528-1534, 1988.

Yannas and Burke, "Design of an Artificial Skin, I. Basic Design Principles," *J. Bio. Mat. Res.* 14:65-81, 1980.

Yannas et al.. "Regeneration of Sciatic Nerve Across 15 mm Gap by Use of Polymeric Template," *Polym. Sci. Technol. Iss. Adv. Biomed. Polymer* 35:109, 1987.

Yannas and Orgill, "Polymeric Template Facilitates Regeneration of Sciatic Nerve Across 15 MM Gap," Polymer *Material Sci. Eng.* 53:216-2198, 1985.

Yannas and Orgill, "Artificial Skin: A Fifth Route to Organ Repair and Replacement," *Iss. Polym. Biomaterial Sci. Eng.* 53:216-218, 1985.

Yannas et al., "Suppression of in Vivo Degradability and of Immunogenicity of Collagen by Reaction with Glycosaminoglyans," *Polymer. Prepar. Am. Chem. Soc. Div. Polym. Chem.* 16(2):209-214, 1975.

Yannas et al., "Wound Tissue Can Utilize a Polymeric Template to Synthesize a Functional Extension of Skin," *Science* 53:221-230, 1982.

Yannas, "What Criteria Should be Used for Designing Artificial Skin Replacement and How Well do the Current Grafting Material Meet These Criteria?" *J. Trauma* 24(9):S29-S39, 1984.

Zund et al., "A New Approach for a Bioprothetic Heart Valve," Eur. Assoc. Cardio-Thoracic Surg., 1995.

Report of the International Reflux Study Committee "Medical Versus Surgical Treatment of Primary Vesicoureteral Reflux: A Prospective International Relflux Study in Children," *J. Urology* 125:277-283, 1981.

\* cited by examiner

TISSUE ENGINEERED TENDONS AND LIGAMENTS

CROSS-REFERENCE TO RELATED APPLICATIONS

This application is a divisional of U.S. application Ser. No. 10/913,769, filed Aug. 6, 2004, now abandoned, which is a continuation of U.S. application Ser. No. 09/670,051, filed Sep. 25, 2000, now U.S. Pat. No. 6,840,962, which is a divisional of U.S. application Ser. No. 08/905,491, filed Aug. 4, 1997, now U.S. Pat. No. 6,123,727, which is a continuation of U.S. application Ser. No. 08/431,780, filed May 1, 1995, now abandoned.

BACKGROUND OF THE INVENTION

The Names of the Parties to a Joint Research Agreement

Massachusetts Institute of Technology and Children's Medical Center Corporation are parties to a joint research agreement.

The present invention is generally in the area of forming new tissues by implantation of appropriate cells on a polymer matrix, and is specifically directed towards construction of new tendons and ligaments.

Tissues connecting bones and muscles are collectively referred to herein as "connective tissue". Tendons are tissues which attach muscles to bones; aponeuroses are sheet-like tendons connecting one muscle with another or with bones; ligaments hold bones together at joints. Tendons and ligaments are elongated, cylindric structures formed of dense connective tissue, adapted for tension in one direction, with fibers having an orderly, parallel arrangement. The most common variety of dense regularly arranged connective tissue has a predominance of collagenous (white) fibers arranged in bundles. Fibroblasts are placed in rows between the bundles. The tissue is silvery white, tough, yet somewhat pliable. The collagen bundles of the tendons aggregate into larger bundles that are enveloped by loose connective tissue containing blood vessels and nerves. Externally, the tendon is surrounded by a sheath of dense connective tissue.

An essential characteristic of connective tissue is its strength and ability to stretch or be pulled, then regain its original shape. When damaged, the orderly structure which imparts this ability to the connective tissue is disrupted and usually does not heal to yield a fully functional tissue.

Tendon defects, regardless of their origin, often prove to be difficult problems for orthopedic surgery and hand surgery. An ideal reconstruction repairs the defect with an autologous tendon graft. Autogenous tendon usage is limited by availability and donor site morbidity. Consequently, other approaches have been used: homo- or heterografts and artificial tendons. Homo- or heterografts, though, suffer from a scarcity of supply, increased susceptibility to infection, and concerns about possible transmission of infectious agents.

A carbon fiber implant for reconstructing severely torn ligaments and tendons has been developed which consists of carbon fibers coated with a polymer such as polylactic acid, as discussed in "Principles of Human Anatomy" by G. J. Tortora, 5th edition (Harper & Row, NY 1989). The coated fibers are sewn in and around torn ligaments and tendons to reinforce them and to provide a scaffolding around which the body's own collagenous fibers grow. The polymer is hydrolysed within the body over time and the carbon fibers eventually fracture, typically within two weeks. During this time, fibroblasts coat the fibers with collagen. The original structure of the tendons is not maintained, however, and the repaired tendon lacks strength and flexibility. Artificial prostheses, although not infectious, are also susceptible to infection, extrusion, and uncertain long-term immunologic interactions with the host. Moreover, prostheses cannot adapt to environmental stresses as do living tendon tissue and have a high incidence of adhesive breakdown at their interface with the host.

It is therefore an object of the present invention to provide a method and materials for creating new tendons and ligaments which have the strength and flexibility of normal tendons and ligaments.

It is a further object of the present invention to provide a method and materials for creating new tendons and ligaments which leaves no foreign materials in the body nor elicits an immunological reaction against the new tendons or ligaments.

SUMMARY OF THE INVENTION

Connective tissue, including neo-tendons and ligaments, has been constructed using biodegradable synthetic scaffolds seeded with tenocytes. The scaffolds are preferably formed from biodegradable fibers formed of a polymer such as polyglycolic acid-polylactic acid copolymers, and seeded with cells isolated from autologous tendon or ligament by means of enzymatic digestion or direct seeding into tissue culture dishes from explants. The cell polymer constructs are then surgically transplanted to replace missing segments of functioning tendon or ligament.

As shown by the examples, transplanted tenocytes attached to biodegradable synthetic polymer scaffolds to generate new tendon in mice. Tenocytes were isolated from freshly slaughtered newborn calf tendon and were seeded onto a non-woven mesh of polyglycolic acid, arranged as either a random array of fibers, or as fibers in parallel. The cell-polymer constructs were implanted into the mice subcutaneously. Specimens were harvested after six to ten weeks and examined. On gross examination, all specimens closely resembled tendons from which the cells had initially been isolated. Histologic evaluation demonstrated that collagen bundles appeared to be organizing in a parallel fashion at the lateral aspects and appeared very similar to the collagen bundles seen in normal tendon. Centrally, the collagen fibrils appeared to be randomly oriented. Specimens that were created from implantation of parallel polymer fibers appeared to have a greater degree of parallel collagen fibril orientation at an earlier time period. The neo-tendon constructs demonstrated moderate tensile strength when stretched.

DETAILED DESCRIPTION OF THE INVENTION

Figure 1:
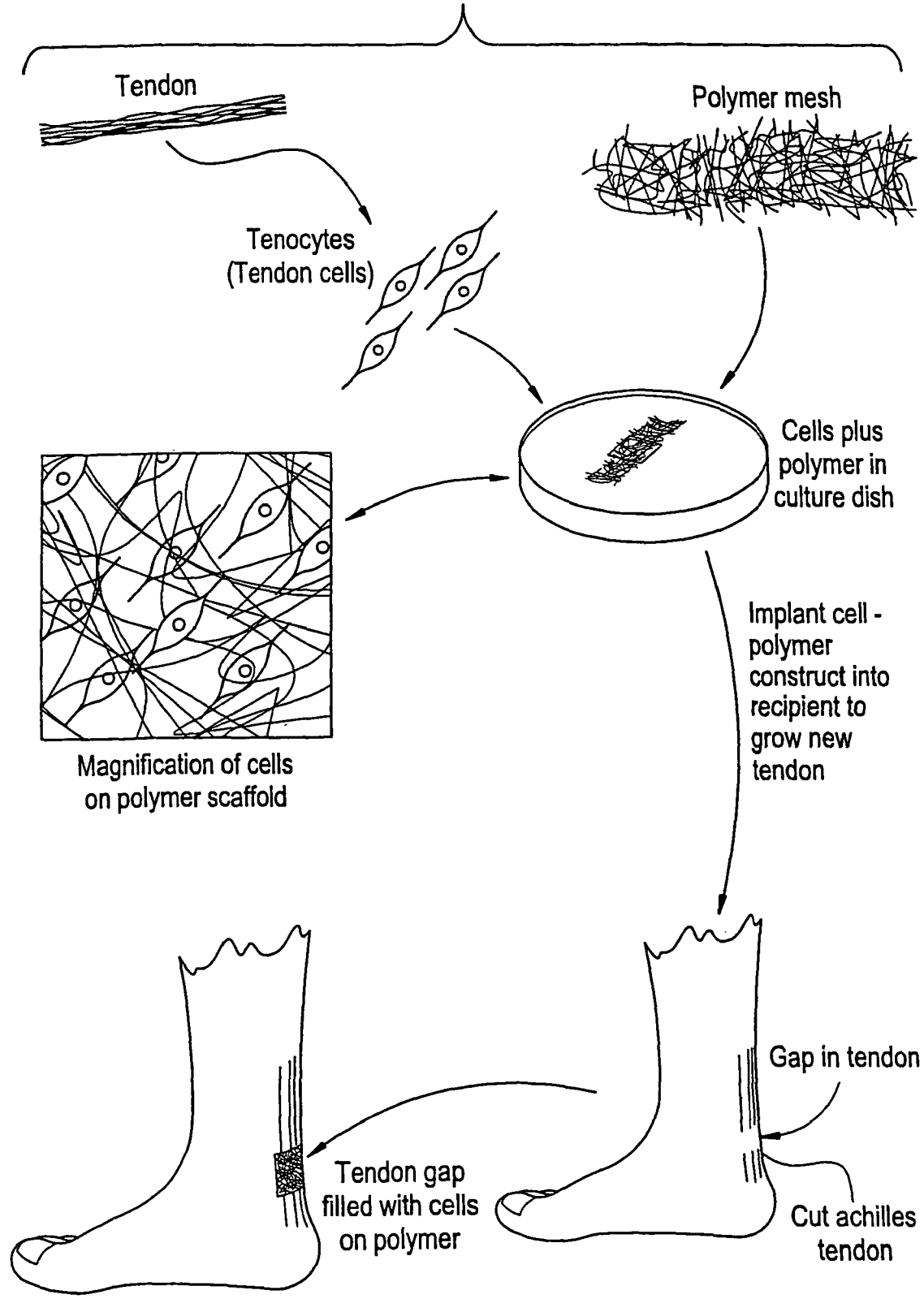
FIG. 1 is a schematic diagram showing the isolation of tenocytes from tendon, the seeding of a polymer with the tenocytes, and the implantation of the cell-polymer construct into a recipient to grow new tendon.

A method and materials to form connective tissue, especially tendons and ligaments, is described wherein cells obtained from tendons (tenocytes) or ligaments (ligamentum cells) are seeded onto and into biodegradable, biocompatible synthetic polymeric fibers, then implanted to form the desired connective tissue.

Cells for Implantation

A variety of cells can be used to form connective tissue. Tenocytes and ligamentum cells are the preferred cells. Fibroblasts differentiate to form collagen and can also be used. Dermal fibroblasts are preferred. Chondrocytes form collagen and can therefore be used, but are not as preferred.

Autologous cells obtained by a biopsy are most preferred. Cells are isolated from autologous tendon or ligament by excision of tissue, then either enzymatic digestion of cells to yield dissociated cells or mincing of tissue to form explants which are grown in cell culture to yield cells for seeding onto matrices. To obtain cells, the area to be biopsied can be locally anesthetized with a small amount of lidocaine injected subcutaneously. Alternatively, a small patch of lidocaine jelly can be applied over the area to be biopsied and left in place for a period of 5 to 20 minutes, prior to obtaining biopsy specimen. The biopsy can be obtained with the use of a biopsy needle, a rapid action needle which makes the procedure extremely simple and almost painless. This small biopsy core of tissue can then be transferred to media consisting of phosphate buffered saline, divided into very small pieces which are adhered to a culture plate, and serum containing media added. Cells are dissociated as described below in the examples using standard techniques, such as treatment with collagenase or trypsin. Alternatively, the tissue biopsy can be minced and the cells dispersed in a culture plate with any of the routinely used medias. After cell expansion within the culture plate, the cells can be passaged utilizing the usual technique until an adequate number of cells is achieved.

They can be maintained and/or proliferated in culture until implanted, either in standard cell culture dishes or after seeding onto matrices, as described below. Alternatively, cells can be seeded into and onto the matrix at the time of implantation.

Polymeric Matrices

Matrix Configuration

For a tendon or ligament to be constructed, successfully implanted, and function, the matrices must have sufficient surface area and exposure to nutrients such that cellular growth and differentiation can occur following implantation. The organization of the tissue may be regulated by the microstructure of the matrix. Specific pore sizes and structures may be utilized to control the pattern and extent of fibrovascular tissue ingrowth from the host, as well as the organization of the implanted cells. The surface geometry and chemistry of the matrix may be regulated to control the adhesion, organization, and function of implanted cells or host cells.

In the preferred embodiment, the matrix is formed of polymers having a fibrous structure which has sufficient interstitial spacing to allow for free diffusion of nutrients and gases to cells attached to the matrix surface until vascularization and engraftment of new tissue occurs. During this period of time, the implanted cells secrete new matrix which includes a parallel arrangement of type 1 collagen fibers as the polymer support scaffolding degrades. The interstitial spacing is typically in the range of 50 to 300 microns. As used herein, "fibrous" includes one or more fibers that is entwined with itself, multiple fibers in a woven or non-woven mesh, and sponge like devices.

Polymers

The matrices are formed of synthetic, biodegradable, biocompatible polymers. The term "bioerodible", or "biodegradable", as used herein refers to materials which are enzymatically or chemically degraded in vivo into simpler chemical species. "Biocompatible" refers to materials which do not elicit a strong immunological reaction against the material nor are toxic, and which degrade into non-toxic, non-immunogenic chemical species which are removed from the body by excretion or metabolism.

In addition to biocompatibility, key characteristics of the polymer are that it must be processable into fibers of an appropriate length, thickness, and strength or use as a matrix that serves to form new tendons or ligaments and it must degrade within the desired time frame, preferably six to twelve weeks, but optionally up to a few months or even a year.

Fibers can be formed by melt-spinning, extrusion, casting, or other techniques well known in the polymer processing area. Preferred solvents, if used, are those which are completely removed by the processing or which are biocompatible in the amounts remaining after processing.

Examples of polymers which can be used include natural and synthetic polymers, although synthetic polymers are preferred for reproducibility and controlled release kinetics. Synthetic polymers that can be used include bioerodible polymers such as poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyamino acids, polyortho esters, polyacetals, degradable polycyanoacrylates and degradable polyurethanes. Examples of natural polymers include proteins such as albumin, collagen, fibrin, and synthetic polyamino acids, and polysaccharides such as alginate, heparin, and other naturally occurring biodegradable polymers of sugar units.

PLA, PGA and PLA/PGA copolymers are particularly useful for forming the biodegradable matrices. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", *Chemistry and Industry*, 905 (1970).

The erosion of the matrix is related to the molecular weights of PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives. A preferred material is poly(lactide-co-glycolide) (50:50), which degrades in about six weeks following implantation (between one and two months).

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

Polymer Coatings

In some embodiments, attachment of the cells to the polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture. A preferred material for coating the polymeric matrix is polyvinyl alcohol or collagen.

Additives to Polymer Matrices

In some embodiments it may be desirable to add bioactive molecules to the cells. A variety of bioactive molecules can be delivered using the matrices described herein. These are referred to generically herein as "factors" or "bioactive factors".

In the preferred embodiment, the bioactive factors are growth factors. Examples of growth factors include heparin binding growth factor (hbgf), transforming growth factor alpha or beta (TGFβ), alpha fibroblastic growth factor (FGF), epidermal growth factor (TGF), vascular endothelium growth factor (VEGF), some of which are also angiogenic factors. In some embodiments it may be desirable to incorporate factors such as nerve growth factor (NGF) or muscle morphogenic factor (MMP). Steroidal antiinflammatories can be used to decrease inflammation to the implanted matrix, thereby decreasing the amount of fibroblast tissue growing into the matrix.

These factors are known to those skilled in the art and are available commercially or described in the literature. In vivo dosages are calculated based on in vitro release studies in cell culture; an effective dosage is that dosage which increases cell proliferation or survival as compared with controls, as described in more detail in the following examples. preferably, the bioactive factors are incorporated to between one and 30% by weight, although the factors can be incorporated to a weight percentage between 0.01 and 30% weight percentage.

Bioactive molecules can be incorporated into the matrix and released over time by diffusion and/or degradation of the matrix, or they can be suspended with the cell suspension.

Implantation

The matrices are implanted in the same manner as other reconstructed or prosthetic tendons or ligaments. They are surgically interposed between the cut ends of autologous tendon and sutured in place with biodegradable suture material.

The tendons and ligaments and other connective tissue are useful for repair and reconstruction of congenital defects as well as traumatic defects. The neo-connective tissue is therefore useful in plastic surgery for cosmetic purposes as well as in reconstructive surgery.

The present invention will be further understood by reference to the following non-limiting examples evaluating the feasibility of transplanted tenocytes attached to biodegradable synthetic polymer scaffolds to generate new tendon in athymic mice. Tenocytes were isolated from freshly slaughtered newborn calf tendon and were seeded onto a non-woven mesh of polyglycolic acid, arranged as either a random array of fibers, or as fibers in parallel. The cell-polymer constructs were implanted into athymic mice subcutaneously. Specimens were harvested after 6-10 weeks and examined. On gross examination, all specimens (n=25) closely resembled tendons from which the cells had initially been isolated after 6 weeks on in vivo incubation. Histologic evaluation using a standard hematoxylin and eosin stain demonstrated polymer remnants of cells embedded within collagen fibrils. The collagen bundle appeared to be organizing in a parallel fashion at the lateral aspects and appeared very similar to the collagen bundle seen in normal tendon. Centrally, the collagen fibrils appeared to be randomly oriented. Specimens that were created from implantation of parallel polymer fibers appeared to have a greater degree of parallel collagen fibril orientation at an earlier time period. The neo-tendon constructs demonstrated moderate tensile strength when stretched.

EXAMPLE 1

Construction of Neo-Tendon

Method and Materials

Sheets approximately 100 microns thick composed of an embossed non-woven mesh of polyglycolic acid with inter-fiber interstitial spacing averaging 75 to 100 microns in diameter, arranged as either a random array of fibers, or as fibers in parallel (Dexon, Davis and Geck), were cut into pieces approximately 0.4 cm×4 cm and set aside. Tendon was obtained from the shoulder of newborn calves within six hours of sacrifice. The tendons were diced into pieces approximately 0.5 cm×0.5 cm and placed in a sterile 50 ml conical tube. The tendon pieces were washed twice with Dulbecco's phosphate buffered saline (PBS) (Gibco, Grand Island, N.Y.). A sterile 0.396 collagenase solution was prepared by mixing 75 mg of type collagenase (Worthington, Freehold, N.J.) with 25 ml of Hamm's F-12 medium (Gibco, Grand Island, N.Y.). The tendon fragments were incubated in the collagenase solution for 12-16 hours at 37° C. on a shaker. After digestion, the solution was filtered through a sterile 150 micron nylon mesh (Tetko, Elmsford, N.Y.) to remove undigested fragments, and the tenocytes were washed twice in 25 ml of PBS. Cells were counted using a hemocytometer and concentrated in a cell suspension containing 150×10 tenocytes/ml. One hundred microliters of suspension (15 million cells) were then seeded onto each of 25 polymer constructs. Cell-polymer constructs were placed into 35 mm tissue dishes with 4 ml of Hamm's F-12 (Tissue Culture Media) with 1096 fetal calf serum (Gibco, Grand Island, N.Y.) with L-glutamine (292 µg/ml), penicillin (100 u/ml), streptomycin (100 µg/ml) and ascorbic acid (50 µg/ml) and kept in an incubator in vitro at 37° C. in the presence of 596 $CO_2$ for one week until the fibers were coated with multiple layers of tenocytes. Then, under general anesthesia, 25 cell-polymer constructs were surgically implanted subcutaneously into each of 25 nude mice (Athymic, NCr/nude/Sde, Dept. of Radiation Medicine at the Massachusetts General Hospital) four to five weeks of age (the experimental group). An additional 10 mice received implants of polymers containing no cells (the control group). Specimens were harvested after six to ten weeks of in vivo incubation and examined grossly and histologically for the evidence of tendon formation. The tensile mechanical property and handling characteristics of each specimen was assessed.

Results

After six weeks, gross examination of all experimental specimens (n=25) closely resembled normal calf tendons from which the cells had been isolated. Histologic evaluation with hematoxylin and eosin and Masson's Trichrome staining demonstrates organized collagen fibrils with polymer remnants. The peripheral areas demonstrated a parallel linear organization of longitudinal collagen fibrils similar to the collagen bundles seen in normal calf tendon. Centrally, however, the collagen fibrils in this early specimens were randomly oriented and lacked the parallel linear organization. At 10 weeks, histological evaluation shows parallel linear organization of collagen bundles throughout the specimens, centrally and peripherally. Specimens created from implantation of tenocytes onto polymer fibers arranged in parallel fashion showed a greater degree of parallel collagen fibril organization at six weeks when compared to specimens created from randomly arranged polymer fibers, control specimens (n=10), without tenocyte implantation showed no evidence of tendon on gross or histological evaluation at ten weeks. Mechanical analysis of neo-tendon constructs have comparable tensile strength and similar mechanical characteristics to normal tendon. Tensile measurements showed that the tissue engineered tendons were very similar in mechanical behavior to that of normal tendons. The average tensile strength of the tissue engineered tendon after eight weeks in vivo was 10.75±2.29 MPa/normal tendon: 32.80±5.21 MPa standard deviation of that of the normal tendons. The mechanical loading was due solely to the new tendons formed, as the polymer scaffolds degrade and loss mechanical strength after four weeks.

The results demonstrate that tenocytes will adhere to synthetic biodegradable polymers survive and multiply in vitro, and that tenocyte-polymer construct implantation in vivo results in formation of tendon with characteristics similar to normal mature tendon. The collagen fibrils undergo organization over time. Histological evaluation of the neo-tendon construct at six weeks shows linear organization, like normal tendon, peripherally and random array of collagen fibrils centrally. With parallel arranged polymer fibers, linear orientation of collagen centrally was achieved at an earlier time. At ten weeks, the collagen fibers were arranged in parallel linear fashion throughout the showed proper anatomic cellular organization regardless of polymer fiber orientation. Thus, parallel structural fibers facilitates early organization of collagen, but the ultimate architectural organization is related to cellular communication and interaction and not of polymer orientation.

Variations and modifications of the present invention will be obvious from the foregoing detailed description of the invention. Such modifications and variations are intended to come within the scope of the following claims.

The invention claimed is:

1. A method of treating a connective tissue defect in a subject comprising implanting into a missing segment of a tendon or ligament of said subject a connective tissue construct comprising:
    (a) a fibrous mesh of synthetic, biodegradable, biocompatible polymer fibers that have an interstitial spacing between approximately 50 and 300 microns; and
    (b) dissociated connective tissue cells implanted in said fibrous mesh in an amount effective to form tendon or ligament.

2. The method of claim 1, wherein said implanting comprises surgically interposing said construct between two ends of autologous tendon or ligament.

3. The method of claim 1, wherein said implanting construct comprises suturing said tendon or ligament.

4. The method of claim 3, wherein said suturing employs biodegradable sutures.

5. The method of claim 1, wherein said connective tissue defect is a congenital defect.

6. The method of claim 1, wherein the said connective tissue defect is caused by a traumatic injury.

7. The method of claim 1, wherein the cells are selected from the group consisting of tenocytes, ligamentum cells, fibroblasts, and chondrocytes.

8. The method of claim 7, wherein said cells are tenocytes.

9. The method of claim 8, wherein said tenocytes are autologous.

10. The method of claim 1, wherein the polymer is selected from the group consisting of poly(lactide), poly(glycolic acid), poly(lactide-co-glycolide), poly(caprolactone), polycarbonates, polyamides, polyanhydrides, polyamino acids, polyorthoesters, polyacetals, degradable polycyanoacrylates, degradable polyurethanes, and polysaccharides.

11. The method of claim 1, wherein said fibrous mesh is suitable for implantation to form tendon.

12. The method of claim 1, wherein said fibrous mesh is suitable for implantation to form ligament.

13. The method of claim 1, wherein said polymer fibers are coated with compounds selected from basement membrane components, agar, agarose, gelatin, gum arabic, collagens types I, II, III, IV and V, fibronectin, laminin, glycosaminoglycans, polyvinyl alcohol, mixtures thereof, and other hydrophilic and peptide attachment materials.

14. The method of claim 13, wherein said polymer fibers are coated with polyvinyl alcohol or collagen.

15. The method of claim 13, wherein said construct further comprises a bioactive molecule.

16. The method of claim 1, wherein said construct further comprises a bioactive molecule.

17. The method of claim 16, wherein said bioactive molecule is selected from the group consisting of heparin binding growth factor, transforming growth factor alpha or beta, alpha fibroblastic growth factor, epidermal growth factor, vascular endothelium growth factor, nerve growth factor, muscle morphogenic factor, and steroidal anti-inflammatories.

18. The method of claim 16, wherein said bioactive molecule comprises 0.01-30% weight percentage of the construct.

19. The method of claim 18, wherein said bioactive molecule comprises 1-30% weight percentage of the construct.

20. The method of claim 1, wherein said cells are autologous cells.

21. The method of claim 1, wherein multiple synthetic fibers in said mesh are woven.

22. The method of claim 1, wherein multiple fibers in said mesh are non-woven.

23. The method of claim 1, wherein said connective tissue construct consists of:
    (a) a fibrous mesh of synthetic, biodegradable, biocompatible polymer fibers that have an interstitial spacing between approximately 50 and 300 microns; and
    (b) dissociated connective tissue cells implanted in said fibrous mesh in an amount effective to form tendon or ligament.

24. The method of claim 1, wherein said connective tissue construct consists of:
    (a) a fibrous mesh of synthetic, biodegradable, biocompatible polymer fibers that have an interstitial spacing between approximately 50 and 300 microns; and
    (b) dissociated connective tissue cells implanted in said fibrous mesh in an amount effective to form tendon or ligament;
wherein said polymer fibers are coated with compounds selected from basement membrane components, agar, agarose, gelatin, gum arabic, collagens types I, II, III, IV and V, fibronectin, laminin, glycosaminoglycans, polyvinyl alcohol, mixtures thereof, and other hydrophilic and peptide attachment materials.

25. The method of claim 1, wherein said connective tissue construct consists of:
   (a) a fibrous mesh of synthetic, biodegradable, biocompatible polymer fibers that have an interstitial spacing between approximately 50 and 300 microns;
   (b) dissociated connective tissue cells implanted in said fibrous mesh in an amount effective to form tendon or ligament; and
   (c) a bioactive molecule.

26. The method of claim 1, wherein said connective tissue construct consists of:
   (a) a fibrous mesh of synthetic, biodegradable, biocompatible polymer fibers that have an interstitial spacing between approximately 50 and 300 microns;
   (b) dissociated connective tissue cells implanted in said fibrous mesh in an amount effective to form tendon or ligament; and
   (c) a bioactive molecule, wherein said polymer fibers are coated with compounds selected from basement membrane components, agar, agarose, gelatin, gum arabic, collagens types I, II, III, IV and V, fibronectin, laminin, glycosaminoglycans, polyvinyl alcohol, mixtures thereof, and other hydrophilic and peptide attachment materials.

\* \* \* \* \*